United States Patent [19]

Kanno et al.

[11] Patent Number: 4,690,920

[45] Date of Patent: Sep. 1, 1987

[54] DERIVATIVE OF CEPHALOSPORANIC ACID AND PHARMACEUTICAL COMPOSITION COMPRISING THE SAME

[75] Inventors: Akihiko Kanno; Shigeaki Muto, both of Tokyo; Koichi Niimura, Sayama; Takao Ando; Takayoshi Fujii, both of Tokyo; Masahiko Fujii, Komae; Takao Furusho, Machida; Chikao Yoshikumi, Kunitachi, all of Japan

[73] Assignee: Kureha Kagaku Kogyo Kabushiki Kaisha, Tokyo, Japan

[21] Appl. No.: 563,515

[22] Filed: Dec. 20, 1983

[30] Foreign Application Priority Data

Dec. 29, 1982 [JP] Japan ................. 57-234550

[51] Int. Cl.$^4$ ................. C07D 501/57; A61K 31/545
[52] U.S. Cl. ................. 514/201; 540/221
[58] Field of Search ................. 544/26, 27, 21; 424/246; 514/201; 540/221

[56] References Cited

U.S. PATENT DOCUMENTS 4,045,437 8/1977 Barth ................. 544/17
4,051,129 9/1977 Shimizu et al. ................. 544/21
4,059,578 11/1977 DeMarinis et al. ................. 544/21
4,395,412 7/1983 Saikawa et al. ................. 424/246

FOREIGN PATENT DOCUMENTS 0075450 3/1983 European Pat. Off. .

2252100 11/1974 France .

Primary Examiner—Nicholas S. Rizzo
Attorney, Agent, or Firm—Oblon, Fisher, Spivak, McClelland & Maier

[57] ABSTRACT

Disclosed herein are a derivative of a substituted cephalosporanic acid, represented by the formula (I):

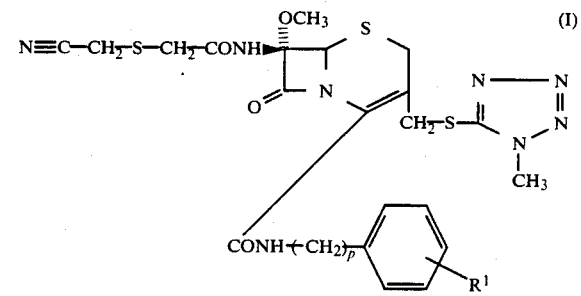

wherein p is 0, 1 or 2 and $R^1$ represents a hydrogen atom, a hydroxyl group, a carbamoyl group, an alkyl group having 1 to 4 carbon atoms or —(CONH)$_m$(CH$_2$)$_n$—COOH wherein m is 0 or 1; n is 0, 1 or 2 and the carboxyl group may have been converted to the salt or the ester thereof, and an antibiotic comprising a derivative of substituted cephalosporanic acid represented by the formula (I).

21 Claims, No Drawings

DERIVATIVE OF CEPHALOSPORANIC ACID AND PHARMACEUTICAL COMPOSITION COMPRISING THE SAME

BACKGROUND OF THE INVENTION

The present invention relates to derivatives of cephalosporanic acid and to pharmaceutical compositions comprising thereof. More in detail, the present invention relates to a series of antibiotics which have been prepared by chemically modifying a substituted cephalosporanic acid having antibacterial activity, and pharmaceutical compositions comprising at least one of the series of the chemically modified, substituted cephalosporanic acid.

The chemically modified, substituted cephalosporanic acid according to the present invention itself has no antibacterial activity, however, after having been absorbed in living body of the host, the anti-bacterial activity is specifically regained In general, antibiotics related to cephalosporins are now broadly used and show a considerably favorable selectivity against bacteria, however, because of the anti-bacterial activity also against the bacterial colonies habitually present in living body, particularly those in the intestines of the host, such antibiotics have a demerit of disturbing the intestinal useful bacterial colonies, particularly when such an antibiotic is orally administered. Such a situation causes the so-called microbisme selectionne et substitue resulting, on some cases, in colitis and diarrhea.

The present inventors have found, as a result of studies in antibiotics without having such a demerit, that the derivatives of a substituted cephalosporanic acid, represented by the following formula (I) are effective in the above-mentioned sense, and have attained the present invention.

Accordingly, the object of the present invention is to provide the derivatives of a substituted cephalosporanic acid, which are useful as the active ingredient of antibiotic composition and do not disturb the intestinal bacterial colonies in the host.

SUMMARY OF THE INVENTION

In the first aspect of the present invention, there is provided a derivative of a substituted cephalosporanic acid, represented by the formula (I):

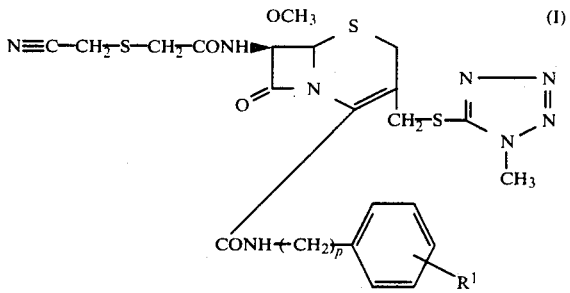

wherein p is 0, 1 or 2 and $R^1$ represents a hydrogen atom, a hydroxyl group, a carbamoyl group, an alkyl group having 1 to 4 carbon atoms or $-(CONH)_m(CH_2)_n-COOH$ wherein m is 0 or 1; n is 0, 1 or 2 and the carboxyl group may have been converted to the salt or the ester thereof.

In the second aspect of the present invention, there is provided a process for producing a derivative of substituted cephalosporanic acid represented by the formula (I):

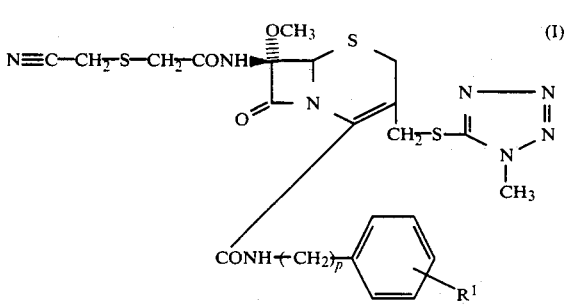

wherein p is 0, 1 or 2 and $R^1$ represents a hydrogen atom, a hydroxyl group, a carbamoyl group, an alkyl group having 1 to 4 carbon atoms or $-(CONH)_m(CH_2)_n-COOH$ wherein m is 0 or 1; n is 0, 1 or 2 and the carboxyl group may have been converted to the salt thereof or the ester thereof, which comprises the step of reacting 7-beta-cyanomethylthioacetamido-7-alpha-methoxy-3-[(1-methyl-1H-tetrazol-5-yl)thio]methyl-cephalosporanic acid represented by the formula (II):

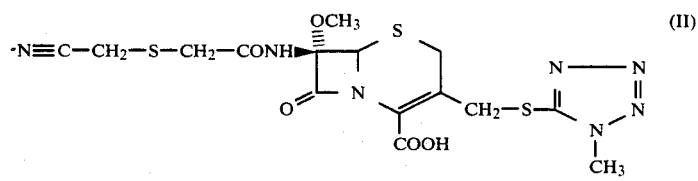

or a derivative thereof with a compound represented by the formula (III):

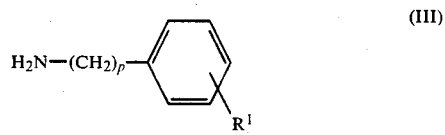

wherein p is 0, 1 or 2 and $R^1$ represents a hydrogen atom, a hydroxyl group, a carbamoyl group or $-(CONH)_m(CH_2)_nCOOH$ wherein m is 0 or 1, n is 0, 1 or 2 and the carboxyl group may have been converted into the salt or the ester thereof, in a solvent for 0.5 to 48 hours at a temperature of −30° to 50° C., thereby obtaining said derivative of a substituted cephalosporanic acid represented by the formula (I).

In the third aspect of the present invention, there is provided an antibiotic comprising a derivative of substituted cephalosporanic acid, represented by the formula:

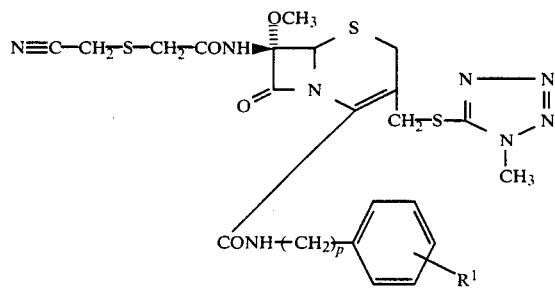

wherein p is 0, 1 or 2 and $R^1$ represents a hydrogen atom, a hydroxyl group, a carbamoyl group, an alkyl group having $C_1$ to $C_4$ or $-(CONH)_m(CH_2)_n-COOH$ wherein m is 0 or 1; n is 0, 1 or 2 and the carboxyl group may have been converted into the salt thereof or the ester thereof.

In the fourth aspect of the present invention, there is provided a pharmaceutical composition in dosage unit form comprising an effective dosage of a derivative of substituted cephalosporanic acid, represented by the formula:

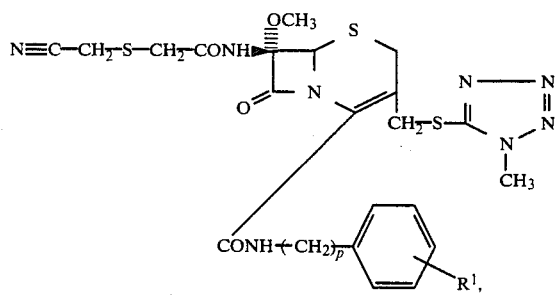

wherein $R^1$ represents a hydrogen atom, a hydroxyl group, a carbamoyl group, an alkyl group having $C_1-C_4$ or $-(CONH)_m(CH_2)_nCOOH$ wherein m is 0 or 1; n is 0, 1 or 2 and a carboxylic group may have been converted into the salt thereof or the ester thereof, and a pharmaceutically acceptable carrier therefor.

In the fifth aspect of the present invention, there is provided a method for the treatment of infectious diseases caused by bacteria which comprises administering an effective amount of a derivative of substituted cephalosporanic acid, represented by the formula:

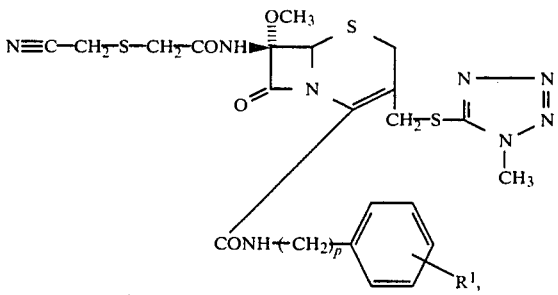

wherein $R^1$ represents a hydrogen atom, a hydroxyl group, a carbamoyl group, an alkyl group having $C_1$-$C_4$ or $-(CONH)_m(CH_2)_nCOOH$ wherein m is 0 or 1; n is 0, 1 or 2 and a carboxylic group may have been converted into the salt thereof or the ester thereof.

DETAILED EXPLANATION OF THE INVENTION

One of the characteristics of the present invention is the derivatives of a substituted cephalosporanic acid which are represented by the formula (I):

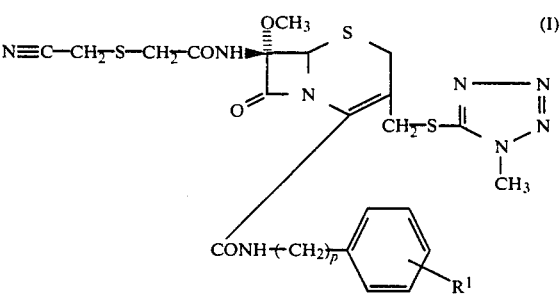

wherein $R^1$ represents a hydrogen atom, a hydroxyl group or an alkyl group of 1 to 4 carbon atoms, a carbamoyl group or a group of $-(CONH)_m(CH_2)_nCOOH$ wherein m is 0 or 1; n is 0, 1 or 2 and a carboxylic group may have been converted into the salt thereof or the ester thereof.

The other of the characteristics of the present invention is the pharmaceutical, antibiotic composition containing at least one of the compounds represented by the formula (I) as the active ingredient thereof.

The compound represented by the formula (I) has been prepared in a process for chemically modifying a substituted cephalosporanic acid, and when the compound represented by the formula (I) is orally administered to the host, it is absorbed into living body of the host without affecting the bacterial colonies habitually present in the intestines and exhibits its antibacterial activity at the first time after entering into the blood of the host. Accordingly, the compound represented by the formula (I) is an antibiotic of a quite new type, and in addition, its acute mammalian toxicity is very low.

The compound represented by the formula (I) may be produced according to the following process comprising reacting 7-beta-cyanomethylthioacetamido-7-alpha-methoxy-3-[(1-methyl-1H-tetrazol-5-yl)thio]methyl-cephalosporanic acid represented by the formula (II):

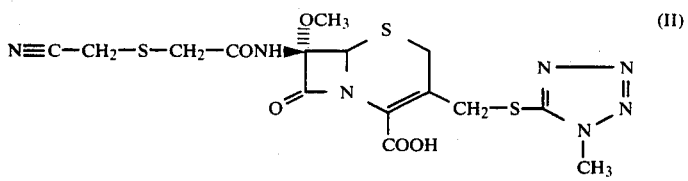

or a derivative thereof with a compound represented by the formula (III):

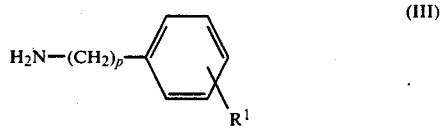

wherein p is 0, 1 or 2 and $R^1$ represents a hydrogen atom, a hydroxyl group, a carbamoyl group or —(-CONH)$_m$(CH$_2$)$_n$COOH wherein m m is 0 or 1; n is 0, 1 or 2 and the carboxyl group may have been converted into the salt or the ester thereof, in an organic solvent, preferably at a temperature of $-30°$ to $50°$ C. for 0.5 to 48 hours.

The compound as a raw material, prepared by modifying the carboxyl group at 4-position of 7-beta-cyanomethylthioacetamido-7-alpha-methoxy-3-[(1-methyl-1H-tetrazol-5-yl)thio]methylcepharosporanic acid represented by the formula (II) into a chemically active group such as acid chloride, acid bromide, acid azide, mixed anhydride of alkylphosphotic acids, mixed anhydride of alkylcarbonic acids, mixed anhydride of aliphatic fatty acids, acid anhydride, active amides, salts of alkali metals, salts of alkaline earth metals, ammonium salt or salt of trimethylamine or dicyclohexylamine,

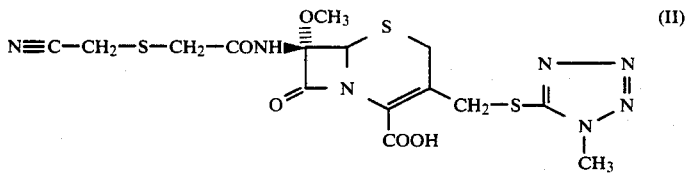

may be used.

In the above-mentioned process, as the compound represented by the formula (III), 4-aminophenylacetic acid, 3-aminophenylacetic acid, 2-aminophenylacetic acid, 4-toluidine, 3-toluidine, 2-toluidine, 4-aminohippuric acid, tyramine, 4-aminobenzoic acid, 3-aminobenzoic acid, 2-aminobenzoic acid, 4-amino-salicylic acid, 3-aminosalicylic acid, 2-aminosalicylic acid, 6-aminonicotinic acid, 2-aminonicotinic acid and the salts and esters thereof may be mentioned including the hydrochlorides and hydrobromides thereof of the amino group thereof. As the solvent, although an organic solvent such as acetone, tetrahydrofuran, benzene, dichloromethane, ethylene dichloride, dioxane, acetonitrile, chloroform, ethyl acetate, ethyl formate, diethyl ether, dimethylforamide or the like may be used, however, every solvent may be used unless it participates in the reaction and a water-soluble solvent among the above-mentioned solvents may be used as a mixture with water.

In addition, it is preferable to add a compound selected from the group consisting of carbodiimide, ethyl chlorocarbonate, ethyl chloroformate, oxalyl chloride, quinoline, an alkali metal hydrogencarbonate, trialkylamine, dialkylaniline and pyridine into the above-mentioned reaction system. In some cases, wherein such a compound shown above is used, the compound represented by the formula (II) may be directly reacted with the compound represented by the formula (III) as will be shown in Examples 3, 4 and 5.

After the reaction is over, after removing the protective group on the amino group of the product if necessary, the objective product is collected from the reaction system by the technique such as washing with a solvent, extracting with a solvent, separating while using a chromatographic column, re-precipitating, distilling the solvent, crystallizing (including recrystallizing), etc.

In the case where $R^1$ is the group —(CONH)$_m$(CH$_2$)$_n$COOH, the pharmaceutical acceptable salts or (C$_1$–C$_4$) alkyl ester of the compound represented by the formula (I) may be used.

Furthermore, in the above-metnioned case, an alternative process may be adopted in which a compound having the group —(CONH)$_m$(CH$_2$)$_n$COOH as $R^1$ in the formula (I) is prepared at first and then the thus obtained compound is derived to the salt or ester.

The pharmacological properties of the compound represented by the formula (I) were investigated as follows:

(1) Acute mammalian toxicity

The acute mammalian toxicity of the compounds represented by the formula (I) was investigated by respectively administering a series of suspension of each of the compounds represented by the formula (I) in aqueous physiological saline solution orally and intraperitoneally into each group of ICRJCL mice and observing the mortality of the thus treated mice for 7 days. The thus obtained cumulative mortality was applied to the Litchfield-Wilcoxon's graphical method to obtain the LD$_{50}$ values. The thus obtained LD$_{50}$ value due to intraperitoneal administration of each of the compounds represented by the formula (I) was higher than 10 g/kg body weight of a mouse (in average).

(2) Effects on the intestinal bacteria

After collecting the feces of a group of mice, each of the compounds represented by the formula (I) was orally administered to each of the group for 2 continued days at a daily dose rate of 500 mg per kg body weight, and the feces were again collected one day after the administration. Each portion of the thus collected, two kinds of the feces was cultured at 25° C. or 37° C. in a variety of culture media for one to five days to see the state of growth of the following bacteria which are present habitually in the intestine of the mouse: *Escherichia coli, Pseudomonas aeruginosa,* a streptococcus bacterial species, a lactobacillis bacteria, *Lactobacillus bifidus* and a bacterioides bacteria.

As a result, the number of each species of bacteria in the cultured medium containing the feces collected after administering each of the compounds represented by the formula (I) was substantially the same as the number of each species of bacteria in the cultured medium containing the feces collected before administering each of the compounds represented by the formula (I), and accordingly, it was verified that each of the compounds represented by the formula (I) did not affect the growth and survival of the tested species of intestinal bacteria.

(3) Antibacterial activity 3-1: The minimum growth-inhibiting concentration (MIC) of each of the compounds represented by the formula (I) was measured according to the standard procedures of Japan Society of Chemotherapy against each of the following bacterial species:

*Escherichia coli,* IFO 12734 and
*Staphylococcus aureus,* IAM 1011

As will be seen in Table 2 of Example 8, each of the compounds represented by the formula (I) showed a MIC which was the same or larger than 100 micrograms/ml, the data corresponding to the result of the test in (2).

3-2: The specific property of each of the compounds represented by the formula (I) that each of the compounds represented by the formula (I) is activated to be antibiotic after having been absorbed into living body of the host was verified by the following test:

On each flat culture plate prepared by adding $10^8$ cells/ml of a preliminarily cultured *Staphylococcus aureus* IAM 1011 into 50 times by weight of Mueller-Hinton's agar culture medium, a penicillin cup of 8 mm in diameter was placed, and into each cup 0.1 ml of each of the compounds represented by the formula (I) or 0.1 ml of a cultured product of each of the compounds represented by the formula (I) together with a rat liver homogenate (containing a metabolism-activating enzyme, referred to as S-9 mix) was introduced. The diameter of each growth-inhibition circle formed around the cup after incubating the flat culture plate with the cup for 18 hours at 37° C. was measured, and the thus obtained value was compared to the value obtained by the same procedures except for using the compound represented by the formula (II), the starting compound instead of each of the compounds represented by the formula (I).

As the results, the diameter of the growth-inhibiting circle due to each of the compounds represented by the formula (I) was zero, and that due to the cultured product of each of the compounds represented by the formula (I) together with S-9 mix was 0 to 33% of that due to the compound represented by the formula (II). The result shows that some of the compounds represented by the formula (I) will be activated after having absorbed into living body of the host to which the compound represented by the formula (I) has been orally administered.

3-3: The activation of the compound represented by the formula (I) in living body was verified by the test of treating an infectious disease caused by bacteria on mice as follows:

Each of 20 mice of a group was infected by intraperitoneal inoculation of *Escherichia coli* IFO 12734 or *Staphylococcus aureus* IAM 1011, and just after or after 4 hours of the inoculation, each of the compounds represented by the formula (I) was orally administered to the inoculated mouse at a dose rate of 500 mg/kg body weight. By observing the mortality of the thus treated mice for 7 days, it was found that while all the mice of the group inoculated but not administered with the compound represented by the formula (I) died on the second day of inoculation, the mortality of the mice inoculated and administered with every one of the compounds represented by the formula (I) was less than 60% showing the effectiveness of the compounds represented by the formula (I) as an anti-infectious disease agent.

As has been stated above, the compound represented by the formula (I) can be said to be a new type of antibiotic which is safe, has no effects on the intestinal bacteria of the host and is converted to an active form against infectious bacteria.

Since the compound represented by the formula (I) is converted to an antibiotic derivative of cephalosporin after having entered in living body of the host, the compound represented by the formula (I) can be used as an antibiotic in the same field wherein the conventional antibiotic derived from cephalosporins, in other words, the compound represented by the formula (I) has the same effect as CEFMETAZOLE ®.

The compound represented by the formula (I) can be used as at least one active ingredient of the pharmaceutical composition in dosage unit form, which contains a pharmaceutically acceptable carrier, diluent or adjuvant (in the case where the compound represented by the formula (I) takes a form of a salt or an ester, the salt or the ester should be the one which is pharmaceutically acceptable).

Such a pharmaceutical composition can be administered orally, injectionally or rectally. Oral administration may be carried out in the form of tablets, capsules, powder, granules, pills and ampoules. These compositions contain a filler, extender binder, wetting agent, disintegrator, dissolution retarder, accerator for reabsorption, adsorbing carrier and lubricant.

As the concrete adjuvant, starch, mannitol, silicic acid, derivatives of cellulose, gelatin, arginate salts, glycerol, agar, calcium carbonate, sodium hydrogencarbonate, paraffin, quarternary ammonium compounds, glycerol monostearate, kaolin, bentonite, talc, potassium stearate, magnesium stearate and polyethylene glycol may be mentioned.

In addition, the pharmaceutical composition comprising the compound represented by the formula (I) takes a form of pharmaceutically acceptable such as emulsion, solution and suspension.

The suppository comprising the compound represented by the formula (I) may contain polyethylene glycol, fatty acid and/or the ester thereof.

Of the pharmaceutical compositions, syrup and elixir contain an inert diluent such as water and paraffin, and may be used as a liquid composition suitable for oral administration. They may contain, in addition, an adjuvant such as wetting agent, sweetener and seazoning.

The composition used for injective administration should be aseptic and may be an aqueous- or non-aqueous solution, suspension or emulsion, and in addition, may contain propylene glycol, polyethylene glycol and olive oil.

The pharmaceutical composition may contain at least one of the compound represented by the formula (I) in an amount of 0.01 to 99.5% by weight, usually 0.1 to 90% by weight thereof.

The compound represented by the formula (I) is used for the same purpose as that of the conventional antibiotics derived from cephalosporins and is effective in the treatment of infectious diseases caused by bacteria. The dose rate of the pharmaceutical composition depends on the degree of infection and the state of the patient, however, generally, 0.1 to 10 g as the active ingredient thereof is daily administered after dividing into portions.

The present invention will be more precisely explained while referring to Examples as follows.

However, the present invention is not restricted to Examples under mentioned. From the foregoing description, one skilled in the art can easily ascertain the essential characteristics of the present invention, and without departing from the spirit and scope thereof, can make various changes and modifications of the invention to adapt it to various usages and conditions.

EXAMPLE 1

Production of N-(4-carboxyphenyl)-{7-beta-cyanomethylthioacetamido-7-alpha-methoxy-3-[(1-methyl-1H-tetrazol5-yl)thio]methyl-3-cepheme-4-carboxylic}amide After three drops of pyridine were added to a suspension of 493.5 mg of sodium 7-beta-cyanomethylthioacetamido-7- alpha-methoxy-3-[(1-methyl-1H-tetrazol-5-yl)thio]methyl-3-cepheme-4-carboxylate in 10 ml of acetone, 217 mg of ethyl chlorocarbonate were added to the thus treated suspension, and the mixture was stirred for 30 min at 0° C. Into the thus stirred mixture, 137 mg of 4-aminobenzoic acid were added to the mixture, and the whole mixture was stirred for 24 hours at 20° C. After the reaction was over, the solvent was distilled off from the reaction mixture, and after adding 30 ml of aqueous 1% solution of sodium hydrogencarbonate to the residue, the residue was extracted three times with each 30 ml of ethyl acetate. After combining the extracts and washing thereof with 30 ml of aqueous 0.1 N hydrochloric acid solution, the layer of ethyl acetate was dried on anhydrous sodium sulfate and filtered through a sheet of filter paper. The thus obtained filtrate was dried under a reduced pressure to be a crude product, which was recrystallized from a mixture of ethyl acetate and n-hexane to obtain 50 mg of crystals melting at 101° to 104° C. in a yield of 8% as the final product showing an ultraviolet absorption maximum at 270 nm in methanol.

The elementary analytical data of the objective product are shown as follows:

|  | C (%) | H (%) | N (%) |
|---|---|---|---|
| Found: | 44.9 | 3.41 | 19.1 |
| Calcd. as $C_{22}H_{20}N_8O_6S_3$: | 44.89 | 3.42 | 19.04 | representing the chemical structure as follows;

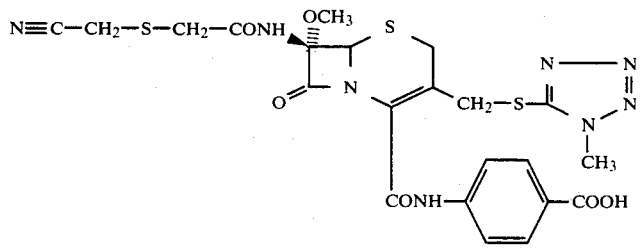

EXAMPLE 2

Production of N-(4-carbomethoxyphenyl)-{7-beta-cyanomethylthioacetamido-7-alpha-methoxy-3-[(1-methyl-1H-tetrazol-5-yl)thio]methyl-3-cepheme-4-carboxylic}amide In quite a similar manner to that in Example 1, the objective product was obtained in an amount of 185 mg from 493.5 mg of sodium 7-beta-cyanomethylthioacetamido-7-alphamethoxy-3-[(1-methyl-1H-tetrazol-5-yl)thio]methyl-3-cepheme-4-carboxylate and 151 mg of methyl 4-aminobenzoate in the presence of 3 drops of pyridine and 217 mg of ethyl chlorocarbonate in a reaction time of 15 hours. The objective product showed a melting point of 104° to 106° C., an ultraviolet absorption maximum at 270 nm in methanol and the following elementary analytical data:

|  | C (%) | H (%) | N (%) |
|---|---|---|---|
| Found: | 45.7 | 3.6 | 18.4 |
| Calcd. as $C_{23}H_{22}N_8O_6S_3$: | 45.84 | 3.68 | 18.59 | representing the chemical structure as follows:

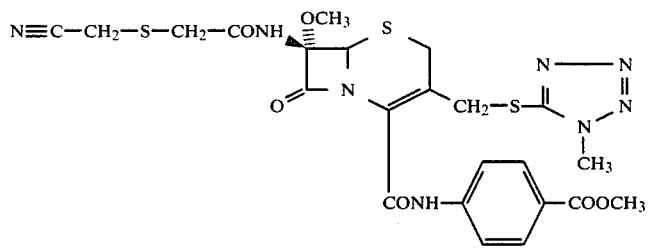

EXAMPLE 3

Production of
N-(4-carbomethoxymethylphenyl)-{7-betacyanomethylthioacetamido-7-alpha-methoxy-3-[(1-methyl-1H-tetrazol-5-yl)thio]methyl-3-cepheme-4-carboxylic}amide Into 100 ml of tetrahydrofuran, 4.71 g of 7-beta-cyanomethylthioacetamido-7-alpha-methoxy-3-[(1-methyl-1H-tetrazol-5-yl)thio]methyl-3-cepheme-4-carboxylic acid, 1.65 g of methyl 4-aminophenylacetate and 2.10 g of N,N'-dicyclohexylcarbodiimide were dissolved, and the thus formed solution was stirred for 24 hours at 20° C. After removing the thus formed dicyclohexylurea by filtration, the solvent was distilled off from the filtrate, and the residue was dissolved in 100 ml of chloroform. After washing the chloroform solution two times with aqueous 5% hydrochloric acid solution and then two times with water, the solvent was distilled off from the solution and the residue was recrystallized from a mixture of ethyl acetate and n-hexane to obtain 1.6 of white powdery crystals melting at 84° to 86° C. in a yield of 25%. The thus obtained objective product showed an infrared absorption spectrum as KBr tablet with the following absorption maxima (cm$^{-1}$): 3350, 2280, 1779, 1740, 1680 and 1530 and the following ultraviolet absorption maxima in methanol: 242 and 270 nm.

The elementary analytical data of the objective product are shown below:

|  | C (%) | H (%) | N (%) |
| --- | --- | --- | --- |
| Found: | 46.5 | 4.3 | 18.2 |
| Calcd. as C$_{24}$H$_{26}$N$_8$O$_6$S$_3$: | 46.60 | 4.21 | 18.21 | representing the chemical structure as follows:

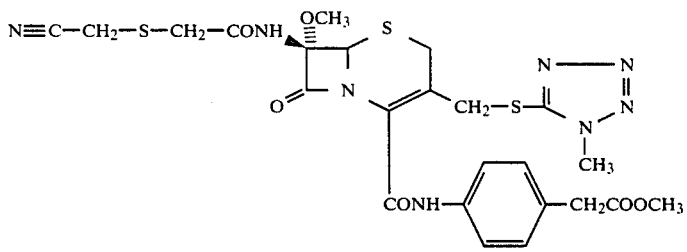

EXAMPLE 4

Production of
N-(4-carbomethoxymethylcarbamoylphenyl)-{7-beta-cyanomethylthioacetamido-7-alpha-methoxy-3-[(1-methyl-1H-tetrazol-5-yl)thio]methyl-3-cepheme-4-carboxylic}amide In quite a similar manner to that in Example 3, the above-mentioned objective compound was obtained in an amount of 422 mg from 471 mg of 7-beta-cyanomethylthioacetamido-7-alphamethoxy-3-[(1-methyl-1H-tetrazol-5-yl)thio]methyl-3-cepheme- 4-carboxylic acid and 208 mg of methyl 4-aminohippurate in the presence of 206 mg of N,N'-dicyclohexylcarbodiimide in 50 ml of tetrahydrofran in a reaction time of 24 hours at 15° C.

The thus obtained objective product showed a melting point of 101° to 103° C. and gave the following elementary analytical data:

|  | C (%) | H (%) | N (%) |
| --- | --- | --- | --- |
| Found: | 46.4 | 4.3 | 19.4 |
| Calcd. as C$_{25}$H$_{25}$N$_9$O$_7$S$_3$: | 46.37 | 4.17 | 19.47 | representing the chemical structure as follows:

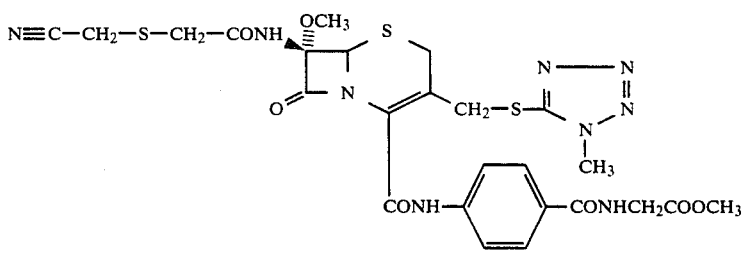

EXAMPLE 5

Production of N-(4-hydroxyphenyl)-{7-beta-cyanomethylthioacetamido-7-alpha-methoxy-3-[(1-methyl-1H-tetrazol-5-yl)thio]methyl-3-cepheme-4-carboxylic}amide Into 100 ml of tetrahydrofuran, 4.71 g of 7-beta-cyanomethylthioacetamido-7-alpha-methoxy-3-[(1-methyl-1H-tetrazol-5-yl)thio]methyl-3-cepheme-4-carboxylic acid, 1.09 g of 4-aminophenol and 2.10 g of N,N'-dicyclohexylcarbodiimide were dissolved, and after stirring the thus formed solution for 24 hours at 25° C., the thus formed dicyclohexylurea was removed from the reaction mixture by filtration, and the solvent was distilled off from the filtrate. After dissolving the distillation residue in 100 ml of chloroform and washing the thus formed solution with aqueous 5% hydrochloric acid solution and water, the solution was dried on anhydrous magnesium sulfate, and the solvent was distilled from the solution. By recrystallizing the distillation residue from a mixture of ethyl acetate and n-hexane, 1.2 g of white crystals melting at 112° to 114° C. were obtained in a yield of 21% as the objective product which showed an infrared absorption spectrum with the following absorption maxima as a KBr tablet: 3350, 2280, 1781, 1670, 1523 and 838 cm$^{-1}$, and showed an ultraviolet absorption spectrum with the following absorption maxima: 241 and 275 nm.

The objective product gave the following elementary analytical data:

|  | C (%) | H (%) | N (%) |
|---|---|---|---|
| Found: | 44.9 | 3.9 | 19.8 |
| Calcd. as $C_{21}H_{22}N_8O_5S_3$: | 44.84 | 3.91 | 19.93 | representing the chemical structure as follows:

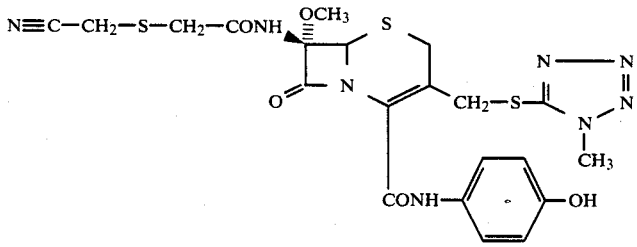

EXAMPLE 6

Production of N-(4-methylphenyl)-{7-beta-cyanomethylthioacetamido-7-alpha-methoxy-3-[(1-methyl-1H-tetrazol-5-yl)thio]methyl-3-cepheme-4-carboxylic}amide In quite a similar manner to that in Example 4, the objective compound was produced in an amount of 432 mg corresponding to a yield of 77%, from 471 mg of sodium 7-beta-cyanomethylthioacetamido-7-alpha-methoxy-3-[(1-methyl-1H-tetrazol-5-yl)thio]methyl-3-cepheme-4-carboxylate and 107 mg of toluidine in the presence of 206 mg of N,N'-dicyclohexylcarbodiimide at a reaction temperature of 20° C. under stirring for 24 hours.

The thus obtained objective product showed a melting point of 95° to 97° C., an infrared absorption spectrum with the following absorption maxima (cm$^{-1}$) as a KBr tablet: 3300, 2925, 2900, 1770, 1600, 1520 and 1380 and an ultraviolet absorption spectrum with the following absorption maxima (nm): 240 and 276.

The elementary analytical data of the objective product were as follows:

|  | C (%) | H (%) | N (%) |
|---|---|---|---|
| Found: | 47.2 | 3.8 | 19.9 |
| Calcd. as $C_{22}H_{22}N_8O_4S_3$: | 47.30 | 3.97 | 20.05 |

EXAMPLE 7

Effect of the compound represented by the formula (I) on the intestinal bacterial colonies Each of the compounds, respectively produced in Examples 1 to 6 was orally administered for two continued days at a daily dosage of 500 mg/kg body weight to each of five female ICR mice of a group after 6 weeks of birth.

Each of the two fecal specimens respectively collected before and after one day of the administration was diluted with 100 times by weight of an anaerobic diluent (a phosphoric buffer solution) and was ground in a mortar, and 0.1 ml of the ground material was smeared on each of the following culture media for the following bacteria and the thus inoculated culture media were incubated under the following conditions. Thereafter, the number of the following bacteria was determined on each culture medium.

| Culture media and conditions of the culture | | |
|---|---|---|
| Bacterial species | Culture medium | Conditions in culture |
| *Escherichia coli* | DHL agar | 37° C., for 1 day, aerobic |
| *Pseudomonas aeruginosa* | NAC agar | 37° C., for 1 day, aerobic |
| a species of Streptococcus | TATAC agar | 37° C., for 1 day, aerobic |
| a species of Lactobacillus | LBS agar | 37° C., for 5 days, anaerobic |
| *Lactobacillus bifidus* | BS agar | 37° C., for 5 days, anaerobic |
| a species of Bacteroides | NBGT agar | 37° C., for 5 days, 7 anaerobic |

The results are shown in Table 1.

TABLE 1

| Fecal specimen | Log₁₀ value of the number of the following bacterial cells/g of feces | | | | | |
|---|---|---|---|---|---|---|
| | Escherichia coli | Pseudomonas aeruginosa | A species of Streptococcus | A species of Lactobacillus | Lactobacillus bifidus | A species of Bacterioides |
| Before administration | 7.0 | <3.0 | 6.4 | 9.0 | 8.0 | 8.1 |
| After administration of Product in Ex. 1 | 7.2 | <3.0 | 6.0 | 8.9 | 8.0 | 8.1 |
| After administration of Product in Ex. 2 | 6.6 | <3.0 | 6.2 | 9.1 | 8.0 | 8.0 |
| After administration of Product in Ex. 3 | 7.1 | <3.0 | 6.0 | 9.1 | 7.9 | 8.0 |
| After administration of Product in Ex. 4 | 7.0 | <3.0 | 5.9 | 9.3 | 7.9 | 8.3 |
| After administration of Product in Ex. 5 | 6.7 | <3.0 | 6.6 | 9.0 | 8.2 | 7.9 |
| After administration of Product in Ex. 6 | 6.9 | <3.0 | 6.3 | 9.2 | 8.0 | 8.0 |
| After administration of CEFMETAZOLE | <3.0 | 7.0 | <3.0 | 4.0 | 3.8 | 4.6 |

As are seen in Table 1, after administration of CEFMETAZOLE, the number of cells of *Escherichia coli* showed an increase as compared to that before administration, and on the other hand, the number of a certain species of Lactobacillus showed a reduction as compared to that before administration.

However, after administration of each of the compounds produced in Examples 1 to 6, the number of each bacterial species showed no noticeable change as compared to that before adminis- tration.

The result shows that each of the compounds produced in Examples 1 to 6 tested did not give any effect on the intestinal bacterial colonies.

EXAMPLE 8

Anti-bacterial activity of the compounds represented by the formula (I)

Anti-bacterial activity of each of the compounds produced in Examples 1 to 6 was measured according to the standard procedures of Japan Society of Chemotherapy in agar plate dilution method as follows:

As a test bacterial species, *Escherichia coli* IFO 12734 and *Staphylococcus aureus* IAM 1011, and each strain was inoculated into Mueller-Hinton's culture medium for 18 to 48 hours at 37° C., and while using the thus cultured bacteria, each of the test bacterial liquid containing 10⁶ cells in one ml was prepared.

Separately, after preparing each series of diluted aqueous solutions of each of the compounds produced in Examples 1 to 6, respectively, each of them was mixed in amount of 1/9 time by weight with the Mueller-Hinton's culture medium and each flat agar culture plate was prepared by using the thus formed mixture.

After smearing each of the test bacterial liquid onto the flat agar culture plate about 2 cm in length while using a platinum loop, the thus inoculated agar plates were incubated for 18 to 24 hours at 37° C. to observe the growth of each bacteria on each agar plate for finding the minimum concentration of each of the compounds produced in Examples 1 to 6 tested which completely inhibited the growth of the inoculated bacteria (minimum concentration of inhibiting the growth of the bacterial species, MIC) The results are shown in Table 2.

TABLE 2

| Specimen: Compound produced in | Unit: microgram/ml Minimum concentration of inhibiting growth of the bacterial species of | |
|---|---|---|
| | Escherichia coli | Staphylococcus aureus |
| Example 1 | ≧100 | ≧100 |
| Example 2 | ≧100 | ≧100 |
| Example 3 | ≧100 | ≧100 |
| Example 4 | ≧100 | ≧100 |
| Example 5 | ≧100 | ≧100 |
| Example 6 | ≧100 | ≧100 |

EXAMPLE 9

Model test for verifying the activation in living body

As a metabolism-activating enzyme, a rat liver homogenate (S-9, manufactured by Oriental Yeast Co.) was used in the following composition (referred to as S-9 mix, hereinafter):

| In 1 ml of composition | 0.5 ml of S-9<br>3.3 micromol of potassium chloride<br>8 micromol of magnesium chloride hexahydrate<br>5 micromol of glucose-6-phosphate<br>4 micromol of NADH<br>4 micromol of NADPH and<br>0.5 ml of 0.2 M phosphoric acid buffer solution of pH of 7.4 |
|---|---|

After mixing 0.1 ml of a solution of the compound to be tested with 0.9 ml of S-9 mix or 0.9 ml of 0.1M phosphoric acid buffer solution, the mixture was subjected to shaking culture for 20 min at 37° C. to prepare a test reaction solution for use in the following experiment.

*Staphylococcus aureus* IAM 1011 was inoculated to Mueller-Hinton's culture medium and the inoculum was cultured for 18 hours at 37° C. and after adjusting the number of the bacterial cells to 10⁸/ml of the culture medium, 50 times by weight of the Mueller-Hinton's agar culture medium were added to the cultured medium to prepare flat culture plates.

After placing a penicillin-cup of 8 mm in diameter on each of the thus prepared flat culture plates, 0.1 ml of the above-mentioned test reaction solution was introduced into the penicillin-cup, and after leaving the system for 2 hours at 4° C., the system was incubated for 18 hour at 37° C., and the diameter of the growth-inhibition circle around the cup on the culture plate was determined.

The thus obtained diameter of the growth-inhibiting circle due to each of the compounds produced respectively in Examples 1 to 6 was compared to that due to the compound repesente by the formula (II), substituted cephalosporanic acid by percentage, and the following signs were respectively given to the respective compounds as follows:

| Sign | Range of percentage |
|------|---------------------|
| −    | 0                   |
| ±    | 0 to 1              |
| +    | 1 to 33             |
| + +  | 33 to 66            |
| + + +| 66 to 100           |

As the results, the signs given to each of the tested present compounds are shown in Table 3.

| Compound obtained in | Sign without adding S-9 mix | Sign with the addition of S-9 mix |
|----------------------|------------------------------|------------------------------------|
| Example 1            | −                            | +                                  |
| Example 2            | −                            | +                                  |
| Example 3            | −                            | ±                                  |
| Example 4            | −                            | +                                  |
| Example 5            | −                            | +                                  |
| Example 6            | −                            | +                                  |

As are seen in Table 3, each of the tested present compounds showed anti-bacterial activity against *Staphylococcus aureus* in vivo to a certain extent only in the presence of S-9 mix. This fact suggests that each of the tested compounds produced in Examples 1 to 6 will become antibiotic after having absorbed in living body of the host to which the compound has been orally administered and subjected to some metabolism.

EXAMPLE 10

Effectiveness in treating experimental infectious diseases (10-1) Against *Escherichia coli*

Cells in number of $1.4 \times 10^8$ of *Escherichia coli* IFO 12734 were intraperitoneally inoculated to each of 40 ddY-SPF mice, and each of 20 mice of the 40 mice was administered two times just after and after 4 hours of the inoculation with each 500 mg of the compound produced in Example 4 per kg of body weight orally, and the other 20 mice were kept untreated. By investigating the presence or absence of the death due to the infection by inoculation of all 60 mice, it was found that all the inoculated and not administered mice died on the second day of inoculation, but in the group of mice administered with the compound produced in Example 4, more than 16 mice were alive even on the 7th day of inoculation.

(10-2) Against *Staphylococcus aureus*

Quite the same experiments as in (10-1) except for intraperitoneously inoculating *Staphylococcus aureus* IAM 1011 in number of $2.3 \times 10^8$ instead of $1.4 \times 10^8$ cells of *E. coli* was carried out by administering two times with each 500 mg of the compound produced in Example 4. As a result, all the 20 mice inoculated and not administered died on the second day of inoculation, however, more than 70% of the inoculated and administered 20 mice were alive even on the 7th day of inoculation.

EXAMPLE 11

Preparation of the pharmaceutical composition (11-1) Preparation of pellets with the following components:
175 mg of the compound produced in Example 1,
16 mg of lactose,
3 mg of hydroxypropylcellulose and
1 mg of magnesium stearate.

The compound produced in Example 1 and lactose were mixed, and after adding an aqueous solution of hydroxypropylcellulose into the mixture, the whole mixture was kneaded, dried and pulverized. After adding magnesium stearate dispersed preliminarily in starch to the pulverized mixture, it was pelletized by an usually method to be pellets each weighing 200 mg.

(11-2) Preparation of a glanular composition with the following component:
176 mg of the compound produced in Example 2,
16 mg of lactose,
4 mg of starch and
4 mg of hydroxypropylcellulose.

The compound produced in Example 2, starch and lactose were mixed, and after adding an aqueous solution of hydroxypropylcellulose to the mixture, the whole mixture was kneaded, dried and pulverized. By sifting the thus pulverized mixture and collecting the fraction passing through #12 Taylor standard mesh and stopping on #48 Taylor standard mesh, the granular composition was obtained.

What is claimed is:

1. A substituted cephalosporin represented by the formula (I):

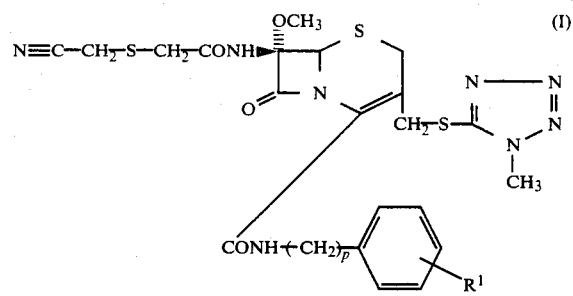

wherein p is 0, 1 or 2 and $R^1$ represents a hydrogen atom, a hydroxyl group, a carbamoyl group, an alkyl group having 1 to 4 carbon atoms, $-(CONH)_m(CH_2)_n-COOH$ wherein m is 0 or 1 and n is 0, 1 or 2, carboxylic ester or carboxylic salt thereof.

2. A substituted cephalosporin according to claim 1, represented by the formula:

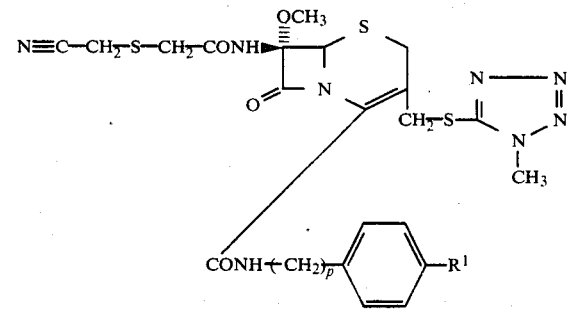

wherein p is 0, 1 or 2 and R¹ represents a hydroxyl group, an alkyl group having 1 to 4 carbon atoms —(CONH)$_m$(CH$_2$)$_n$COOH wherein m is 0 or 1 and n is 0, 1 or 2, carboxylic (C$_1$–C$_4$) alkyl ester or salt thereof.

3. N-(4-carboxyphenyl)-{7-beta-cyanomethylthioacetamido-7-alpha-methoxy-3-[(1-methyl-1H-tetrazol-5-yl)thio]methyl-3-cepheme-4-carboxylic}amide.

4. N-(4-carbomethoxyphenyl)-{7-beta-cyanomethylthio acetamido-7-alpha-methoxy-3-[(1-methyl-1H-tetrazol-5-yl)thio]methyl-3-cepheme-4-carboxylic}amide.

5. N-(4-carbomethoxymethylcarbamoylphenyl)-{7-beta cyanomethylthioacetamido-7-alpha-methoxy-3-[(1-methyl-1H- tetrazol-5-yl)thio]methyl-3-cepheme-4-carboxylic}amide.

6. N-(4-hydroxyphenyl)-{7-beta-cyanomethylthioacetamido-7-alpha-methoxy-3-[(1-methyl-1H-tetrazol-5-yl)thio]methyl-3-cepheme-4-carboxylic}amide.

7. N-(4-methylphenyl)-{7-beta-cyanomethylthioacetamido--alpha-methoxy-3-[(1-methyl-1H-tetrazol-5-yl)thio]-methyl-3-cepheme-4-carboxylic}amide.

8. A pharmaceutical antibiotic composition in dosage unit form comprising an antibiotically effective dosage of a substituted cephalosporin represented by the formula:

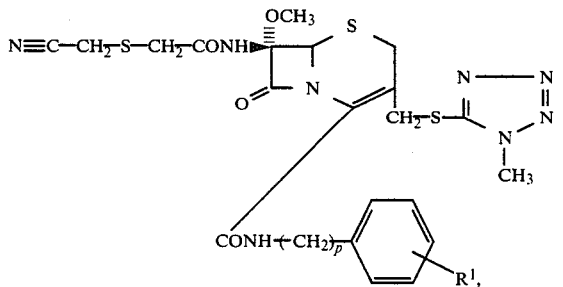

wherein p is 0, 1 or 2, R¹ represents a hydrogen atom, a hydroxyl group, a carbamoyl group, an alkyl group having C$_1$–C$_4$, —(CONH)$_m$(CH$_2$)$_n$COOH wherein m is 0 or 1 and n is 0, 1 or 2, carboxylic or carboxylic salt ester thereof, and a pharmaceutically acceptable carrier therefor.

9. A pharmaceutical antibiotic composition according to claim 8, wherein said substituted cephalosporin is represented by the formula:

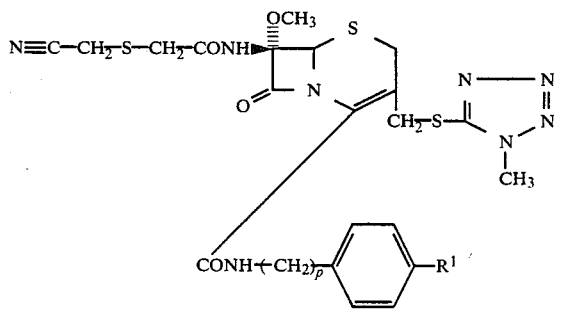

wherein p is 0, 1 or 2 and R¹ represents a hydroxyl group, an alkyl group having 1 to 4 carbon atoms, —(CONH)$_m$(CH$_2$)$_n$COOH wherein m is 0 or 1 and n is 0, 1 or 2, (C$_1$–C$_4$) alkyl ester or carboxylic salt thereof.

10. A pahrmaceutical antibiotic composition according to claim 9, wherein said substituted caphalosporin is N-(4 -carboxyphenyl)-{7-beta-cyanomethylthioacetamido-7- alpha-methoxy-3-[(1-methyl-1H-tetrazol-5-yl)thio]methyl-3- cepheme-4-carboxylic}amide.

11. A pharmaceutical antibiotic composition according to claim 9, wherein said substituted cephalosporin is N-(4-carbomethoxyphenyl)-{7-beta-cyanomethylthioacetamido-7- alpha-methoxy-3-[(1-methyl-1H-tetrazol-5-yl)thio]methyl-3- cepheme-4-carboxylic}amide.

12. A pharmaceutical antibiotic composition according to claim 9, wherein said substituted cephalosporin is N-(4-carbomethoxymethylcarbamoylphenyl)-{7-beta-cyanomethylthioacetamido-7-alpha-methoxy-3-[(1-methyl-1H-tetrazol-5-yl)thio]methyl-3-cepheme-4-carboxylic}amide.

13. A pharmaceutical antibiotic composition according to claim 9, wherein said substituted cephalosporin is N-(4-hydroxyphenyl)-{7-beta-cyanomethylthioacetamido-7- alpha-methoxy-3-[(1-methyl-1H-tetrazol-5-yl)thio]methyl-3- cepheme-4-carboxylic}amide.

14. A pharmaceutical antibiotic composition according to claim 9, wherein said substituted cephalosporin is N-(4-methylphenyl)-{7-beta-cyanomethylthioacetamido-7-alpha- methoxy-3-methyl-[1H-tetrazol-5-yl)thio]methyl-3-cepheme-4- carboxylic}amide.

15. A method for the treatment of infectious diseases caused by bacteria which comprises administering an antibiotically effective amount of a substituted cephalosporin, represented by the formula:

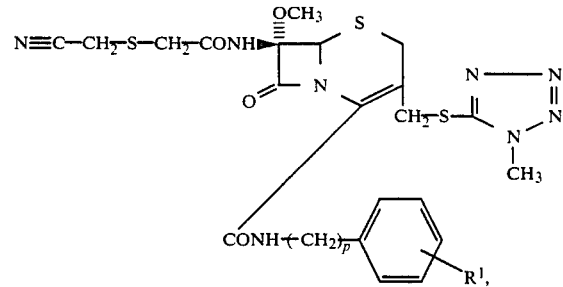

wherein p is 0, 1 or 2, R¹ represents a hydrogen atom, a hydroxyl group, a carbamoyl group, an alkyl group having C$_1$–C$_4$—(CONH)$_m$(CH$_2$)$_n$COOH wherein m is 0 or 1 and n is 0, 1 or 2, carboxylic or carboxylic salt ester thereof.

16. A method for treatment according to claim 15, wherein said substituted cephalosporin is represented by the formula:

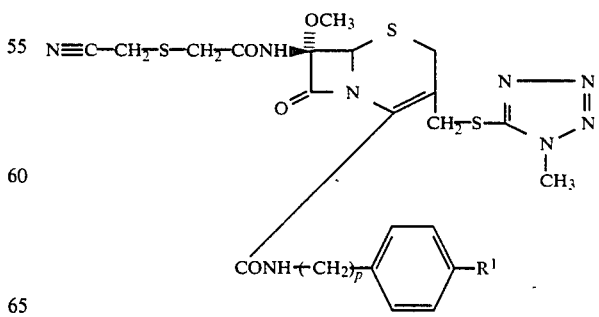

wherein p is 0, 1 or 2 and R¹ represents a hydroxyl group, an alkyl group having 1 to 4 carbon atoms, —(-

CONH)$_m$(CH$_2$)$_n$COOH wherein m is 0 or 1 and n is 0, 1 or 2, (C$_{1-C4}$) alkyl ester or carboxylic salt thereof.

17. A method for treatment according to claim 16, wherein said substituted caphalosporin is N-(4-carboxyphenyl)-{7-beta-cyanomethylthioacetamido-7-alpha-methoxy-3-[(1-methyl-1H-tetrazol-5-yl)thio]methyl-3-cepheme-4- carboxylic}amide.

18. A method treatment according to claim 16, wherein said substituted cephalosporin is N-(4-carbomethoxyphenyl)-{7-beta-cyanomethylthioacetamido-7- alpha-methoxy-3-[(1-methyl-1H-tetrazol-5-yl)thiolmethyl-3- cepheme-4-carboxylic}amide.

19. A method for treatment according to claim 16, wherein said substituted cephalosporin is N-(4-carbomethoxymethylcarbanoylphenyl)-{7-beta-cyanomethyl- thioacetamido-7-alpha-methoxy-3-[(1-methyl-1H-tetrazol-5-yl)thio]- methyl-3-cepheme-4-carboxylic}amide.

20. A method for treatment according to claim 16, wherein said substituted cephalosporin is N-(4-hydroxyphenyl)-{7-beta-cyanomethylthioacetamido-7-alpha-methoxy-3-[(1-methyl-1H-tetrazol-5-yl)thio]methyl-3-cepheme-4-carboxylic}amide.

21. A method for treatment according to claim 16, wherein said substituted cephalosporin is N-(4 methylphenyl)-{7-beta-cyanomethylthioacetamido-7- alpha-methoxy-3-[(1-methyl-1H-tetrazol-5-yl)thio]methyl-3-cepheme-4-carboxylic}amide.

* * * * *

UNITED STATES PATENT AND TRADEMARK OFFICE
CERTIFICATE OF CORRECTION

PATENT NO. : 4,690,920
DATED : SEPTEMBER 1, 1987
INVENTOR(S) : AKIHIKO KANNO ET AL

It is certified that error appears in the above—identified patent and that said Letters Patent is hereby corrected as shown below:

Amend formula (I) in column 2,

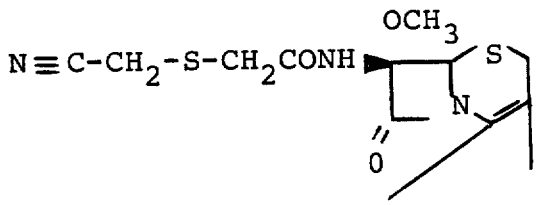

to read as follows:

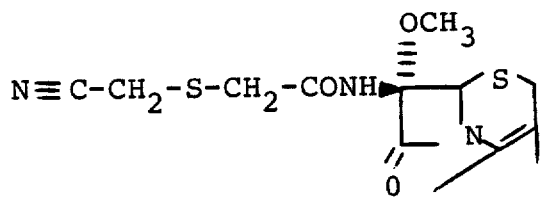

Amend "$C_1 14$" in column 4, line 16, to read as --$C_1$-- --.

Amend "ICRJCL" in column 6, line 55, to read as --ICR-JCL--.

UNITED STATES PATENT AND TRADEMARK OFFICE
CERTIFICATE OF CORRECTION

PATENT NO. : 4,690,920

DATED : SEPTEMBER 1, 1987

INVENTOR(S) : AKIHIKO KANNO ET AL

It is certified that error appears in the above-identified patent and that said Letters Patent is hereby corrected as shown below:

Amend "$C_1-C_4-(CONH)_m(CH_2)_nCOOH$" in column 20, line 46, to read --$C_1-C_4,-(CONH)_m(CH_2)_nCOOH$--.

Signed and Sealed this

Nineteenth Day of April, 1988

Attest:

DONALD J. QUIGG

*Attesting Officer*　　　*Commissioner of Patents and Trademarks*